United States Patent [19]

Bunel et al.

[11] Patent Number: 5,288,903
[45] Date of Patent: Feb. 22, 1994

[54] PREPARATION OF 3-PENTENOIC ACID AND A CATALYST THEREFORE

[75] Inventors: Emilio E. Bunel, Wilmington; Chen-Chou Chiang, Hockessin; Michael B. D'Amore; Erik J. Schaumann, both of Wilmington; Leon S. Scott, Wilmington, all of Del.

[73] Assignee: E. I. du Pont de Nemours and Company, Wilmington, Del.

[21] Appl. No.: 93,703

[22] Filed: Jul. 26, 1993

[51] Int. Cl.$^5$ ............................................. C07C 321/00
[52] U.S. Cl. ................................. 562/598; 562/600; 549/3; 549/28
[58] Field of Search ............... 562/598, 600, 592, 590; 549/3, 28; 560/204

[56] References Cited

U.S. PATENT DOCUMENTS

| | | | |
|---|---|---|---|
| 4,611,082 | 9/1986 | Chan et al. | 562/592 X |
| 4,633,015 | 12/1986 | Chan et al. | 562/590 |
| 4,925,973 | 5/1990 | Deneerot et al. | 560/204 |
| 5,081,292 | 1/1992 | Denis et al. | 562/598 X |
| 5,166,421 | 11/1992 | Bruner, Jr. | 562/591 X |

Primary Examiner—Arthur C. Prescott

[57] ABSTRACT

Preparation of 3-pentenoic acid by the reaction of 3-pentenoylchloride, water and butadiene. 3-chloro-1-butene and 1-chloro-2-butene are also formed. Preferably the 3-pentenoylchloride is formed by the reaction of chlorobutene with carbon monoxide using a palladium catalyst.

13 Claims, No Drawings

PREPARATION OF 3-PENTENOIC ACID AND A CATALYST THEREFORE

FIELD OF THE INVENTION

This invention relates to the preparation of 3-pentenoic acid by the reaction of a 3-pentenoylchloride, water, and butadiene in the presence of hydrochloric acid. The resulting mixture contains 3-pentenoic acid and 3-chloro-1-butene and 1-chloro-2-butene. The 3-pentenoylchloride is preferably formed by the reaction of a chlorobutene selected from the group consisting of 3-chloro-1-butene and 1-chloro-2-butene with carbon monoxide using a palladium catalyst. One suitable catalyst has the formula $C_{10}H_{11}O_4PdCl$, and the structural formula:

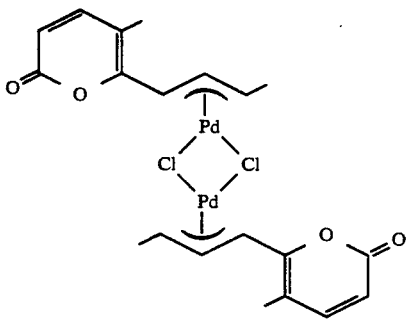

BACKGROUND OF THE INVENTION

The preparation of 1-chloro-2-butene by the reaction of butadiene and hydrogen chloride is taught in U.S. Pat. No. 3,055,954 to Montagna et al.

The reaction of acyl halides with water to form acids is taught in standard organic chemistry textbooks.

The preparation of unsaturated carboxylic acid halides by the reaction of 1-chloro-2-butene (crotyl chloride) and carbon monoxide and a palladium catalyst is taught in U.S. Pat. No. 3,338,961 to Closson et al. See example 8 in particular. In example 5 the patent shows evaporation under vacuum prior to distillation of the product. *Journal of the Chemical Society*, 1964, pages 1588–1594, describes the use of palladium chloride complexes to react 3-chloro-1-butene with carbon monoxide to form 3-pentenoyl chloride. See table 2, page 1589.

3-pentenoic acid is an intermediate in the preparation of adipic acid from butadiene. See Burke U.S. Pat. No. 4,788,333. Adipic acid is a monomer used in the preparation of 6,6 nylon.

It is an object of the present invention to provide a process for the production of 3-pentenoic acid and 3-chloro-1-butene and 1-chloro-2-butene by a process in which less yield loss due to the formation of chlorovaleric acid than is obtained when these desired products are formed in separate reactions.

SUMMARY OF THE INVENTION

The present invention is a process for the simultaneous preparation of 3-pentenoic acid, 3-chloro-1-butene and 1-chloro-2-butene which comprises:

a) combining 3-pentenoylchloride with water, butadiene, and hydrochloric acid to form a mixture where the ratio of butadiene to pentenoylchloride is 1:1 to 6:1 and the molar ratio of water to 3-pentenoylchloride is 1:1 to 15:1, and reacting this mixture at a temperature in the range of about 0 degrees C. to 100 degrees C., preferably 30 to 50 degrees C., and at a pressure of about 50 to 600 psig to form a two phase mixture comprising an organic phase containing 3-pentenoic acid, chlorovaleric acid, 3-chloro-1-butene and 1-chloro-2-butene, and an aqueous phase, b) separating the two phases and separating said chlorobutenes from the organic phase by distillation, c) separating 3-pentenoic acid from the organic phase by distillation.

The present invention also includes the preparation of 3-pentenoylchloride used to prepare 3-pentenoic acid, and thus is a process for the preparation of 3-pentenoic acid which comprises:

a) reacting a chlorobutene selected from the group consisting of 3-chloro-1-butene, and 1-chloro-2-butene, and carbon monoxide in the presence of 0.05 to 5 percent by weight of a palladium catalyst at a temperature between 90 and 190 degrees C. and at a carbon monoxide pressure of between 250 and 5,000 psig to form a reaction mixture containing 3-pentenoylchloride, carbon monoxide, 3-chloro-1-butene and 1-chloro-2-butene, b) separating carbon monoxide from the reaction mixture by heating the mixture at a temperature in the range of 100 to 140 degrees C. at a pressure of 25 to 1500 psig, c) separating a mixture containing 3-pentenoylchloride and chlorobutenes from the reaction mixture by distillation, and simultaneously forming $C_{10}H_{11}O_4PdCl$, (This compound is a catalyst, and it is formed in greater or lesser amounts depending on the exact conditions of distillation.)

d) separating and passing $C_{10}H_{11}O_4PdCl$ to step a) above, e) combining the separated mixture containing 3-pentenoylchloride and chlorobutenes with water, butadiene, and hydrochloric acid to form a mixture where the ratio of butadiene to pentenoylchloride is 1:1 to 6:1 and the molar ratio of water to 3-pentenoylchloride is 1:1 to 15:1, and reacting this mixture at a temperature in the range of about 0 degrees C. to 100 degrees C., and at a pressure of about 50 to 600 psig to form a two phase mixture comprising an organic phase containing 3-pentenoic acid, chlorovaleric acid, and additional chlorobutene selected from the group consisting of 3-chloro-1-butene and 1-chloro-2-butene, and an aqueous phase, f) separating the two phases and separating said chlorobutenes from the organic phase by distillation and passing the chlorobutenes to step a) above, g) separating 3-pentenoic acid from the reaction mixture by distilling the mixture.

A preferred catalyst for the process of the invention is $C_{10}H_{11}O_4PdCl$. This catalyst is formed in carrying out the process as follows:

a) reacting a chlorobutene selected from the group consisting of 3-chloro-1-butene and 1-chloro-2-butene, and carbon monoxide in the presence of 0.05 to 5 mole percent by weight palladium catalyst at a temperature between 90 and 190 degrees C. and at a carbon monoxide pressure of between 500 and 5,000 psig. to form a reaction mixture containing 3-pentenoylchloride, carbon monoxide, 3-chloro-1-butene and 1-chloro-2-butene, b) separating carbon monoxide from the reaction mixture by heating the mixture at a temperature in the range of 100 to 140 degrees C. at a pressure of 25 to 1500 psig, c) separating a mixture containing 3-pentenoylchloride and chlorobutene from the reaction mixture by distillation, and simultaneously forming $C_{10}H_{11}O_4PdCl$.

DETAILED DESCRIPTION OF THE INVENTION

The chlorobutene used in the preparation of 3-pentenoylchloride may be a mixture of 3-chloro-1-butene and 1-chloro-2-butene.

The palladium catalyst may be a mixture of palladium compounds. Suitable palladium compounds include: In General: All zerovalent, divalent, or tetravalent Pd compounds are suitable starting catalysts. The following are Examples:

Palladium halides ($PdCl_2$, $PdBr_2$, $PdI_2$, $Na_2PdCl_4$, etc.)
Palladium sulfate
Palladium nitrate
Palladium carboxylates (palladium acetate, etc.)
Palladium sulfonates
Organo palladium complexes (palladium acetylacetonate, bis(bibenzylidene acetone) palladium, etc.)
Pyridyl and pyridyl class palladium complexes
Allylic palladium halides esp crotyl palladium chloride dimer
Palladium cyanide
Alkyl and aromatic phosphine complexes of zero and divalent palladium (tetrakis triphenylphosphine palladium, bistriphenylphosphine palladium dichloride, etc.)
Palladium black
Supported palladium or its compounds (palladium on alumina, silica, clays, sulfates, carbonates, resins, polymers, etc.)
Palladium oxide After forming the reaction mixture containing 3-pentenoylchloride the carbon monoxide is separated from the reaction mixture. This removal is necessary in order to prevent the product from degrading. The carbon monoxide is stripped from the reaction mixture by heating the mixture at low pressure.

The 3-pentenoylchloride and chlorobutenes are then separated from the reaction mixture by distillation preferably at a temperature in the range of about 50 to about 120 degrees C. and at a pressure in the range of about 0.1 to 2 atmospheres. During the distillation, $C_{10}H_{11}O_4PdCl$ forms. This compound has the following structure:

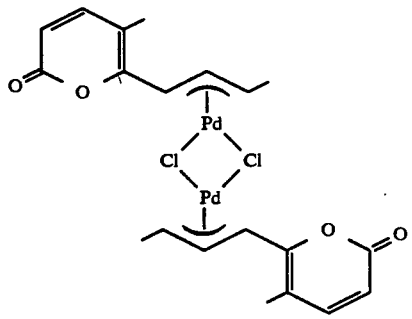

This compound is an effective catalyst for the preparation of 3-pentenoylchloride, and it may be separated from the reaction mixture by filtration, and cycled to the first step of the process. The compound is a green solid. Often the compound is recycled to the first step as part of the residual liquid.

The 3-pentenoylchloride and chlorobutenes are then combined with water, butadiene and hydrochloric acid. The molar ratio of butadiene to 3-pentenoylchloride should be in the range of about 1:1 to 6:1, and the amount of water should be in a molar ratio of 1:1 to 15:1, preferably about 1:1 to 10:1, to the amount of pentenoylchloride. Preferably the reaction is carried out at a temperature in the range of about 30 to 50 degrees C. The formation of 1-chloro-2-butene from the reaction of butadiene and hydrochloric acid proceeds at a faster rate if a catalyst is employed. Suitable catalyst include chlorides bromides, iodides, nitrates sulfates and acetates of such metals as magnesium, aluminum zinc iron cadmium cobalt nickel tin lead copper mercury and the like. See U.S. Pat. No. 3,055,954 to Montagna et al. Preferably cuprous chloride is added to the reaction mixture in an amount of 500 to 20,000 ppm. parts of the reaction mixture.

The product of hydrolysis of pentenoyl chloride will contain varying amounts of 3- or 4-chlorovaleric acid either as a coproduct of hydrolysis or as a result of hydrolysis of chloropentenoyl chloride formed in the carbonylation step. The amount will depend upon a number of factors and could be as much as 5% of the pentenoic acids. A very preferred way of reducing chlorovaleric formation is to catalyze hydrolysis/hydrochlorination with CuCl. However, in any case it is important to remove as much of the chlorovaleric acid from pentenoic acid as possible to prevent chloride contamination during the conversion of 3-pentenoic acid to adipic acid. The chlorovaleric acid can be removed by distillation of pentenoic acid under conditions where chlorovaleric acid decomposes to HCl and valerolactone (see example 5.) The distillation temperature should be in the range of about 180 degrees C. to 220 degrees C., preferably about 200 degrees C. This is desirable since HCl can be returned to the hydrolysis/hydrochlorination reactor and valerolactone is a suitable feed for the conversion to adipic acid. The addition of water to the column is believed to facilitate recovery of the HCl.

EXAMPLE 1

An equilibrium mixture (CB in table 1) of crotyl chloride and 3-chloro-1-butene containing 1500 ppm Pd (from crotyl palladium chloride dimer) was continuously fed to a 50 ml Hastelloy B reactor maintained at 120 C and pressured to 2000 psig with CO. Holdup time in the reactor was 2.85 hrs. The product was continuously collected from the reactor. Conversion to acid chlorides was 27% and selectivity to 2- and 3-pentenoyl chloride was 92 mole %. In a series of runs, holdup time (HUT), catalyst concentration (Pd (ppm)), and temperature were varied and results, selectivity to 2- and 3-pentenoyl chloride (Sel to 2- and 3-PACl) are given in Table 1.

TABLE 1

| Temp C. | Press (PSIG) | HUT (Hours) | Pd (ppm) | CB Conv to Acid Chlorides | Sel to 2- and 3-PACL |
|---|---|---|---|---|---|
| 130 | 2800 | 1.0 | 3750 | 26 | 95 |
| 130 | 2800 | 2.0 | 3750 | 47 | 94 |
| 120 | 1500 | 1.0 | 1500 | 10 | 94 |
| 120 | 1500 | 2.0 | 1500 | 16 | 94 |

TABLE 1-continued

| Temp C. | Press (PSIG) | HUT (Hours) | Pd (ppm) | CB Conv to Acid Chlorides | Sel to 2- and 3-PACL |
|---|---|---|---|---|---|
| 120 | 1500 | 3.0 | 1500 | 20 | 95 |

The products from all the runs in the table were combined. This was fed to a one plate distillation apparatus where chlorobutenes and part of the pentenoyl chloride were distilled away from the catalyst and any high boilers. The pressure of the system was maintained at 200 mm and the final pot temperature was 80 C. A middle cut contained 78% chlorobutenes and 24% pentenoyl chlorides (705 g total). The catalyst containing heel can be recycled to the carbonylation step.

Product from one plate distillations, butadiene and aq HCl (37%) were continuously fed from separate pumps to a 50 ml Hastelloy C autoclave. Nitrogen pressure was maintained at 300 psig and temperature, holdup time and reactant ratios were varied. Results are summarized in Table 2. The major products are the desired 3-pentenoic acid and chlorobutenes which can be recycled to the carbonylation step.

TABLE 2

| Temp | HUT (hr) | H2O/PACl | PACl Conv | BD Conv |
|---|---|---|---|---|
| 28 | 0.5 | 1.6 | 97 | 56 |
| 30 | 0.25 | 1.6 | 90 | 36 |
| 50 | 0.25 | 1.6 | 98 | 52 |
| 50 | 0.25 | 3.4 | 99 | 60 |

EXAMPLE 2

Demonstrating the Advantage of Coproduction of Chlorobutenes and Pentenoic Acid

To a 300 ml Hastelloy autoclave was added 120 g of a mixture containing 25 wgt % pentenoyl chloride and 73 wgt % chlorobutenes. Aqueous HCl (29 wgt % HCl) was added to hydrolyze the pentenoyl chloride to pentenoic acid. After addition of the acid was complete, butadiene was added. Ratios of reactants are given in Table 3. In another run the butadiene was added to the chlorobutene/pentenoyl chloride mixture before the aqueous acid. Results of these runs are in Table 3. Addition of butadiene before the aqueous HCl addition reduces the extent of undesirable chlorovaleric acid by-product formation. In the run where butadiene was added before the acid was added, between 50 and 80 per cent of the butadiene was converted to chlorobutene.

TABLE 3

| Pentenoyl Chloride/ Butadiene/Water (m) | Butadiene Addition | Chlorovaleric Acid Selectivity |
|---|---|---|
| 1/1/3.4 | After Acid | 13.7 |
| 1/1/3.0 | Before Acid | 4.4 |

EXAMPLE 3

(Not a preferred embodiment of the invention—compare with Example 4)

To a Fisher Porter tube (~100 ml Vol), fitted with a dip tube for addition of anhydrous HCl and another dip tube for removal of samples, the following was added:

| 3PA | 50 grams |
|---|---|
| Water | 0.31 grams |

The temperature was controlled by adding heat with an infrared heating lamp. The tube was evacuated and then charged with:

| Butadiene | 38 ml (+ or −2 ml) |
|---|---|

The tube, stirred with a magnetic stirring bar, was then pressured to 140 psi (gage) with anhydrous HCl and maintained at that pressure until the run was completed. Upon addition of the HCl the contents rapidly rose in temperature to 50 degrees C. and was held at that temperature during the run. Samples were removed from the tube at various times and analyzed with the following results where the components are in weight percent:

| | Time (min) | | | | |
|---|---|---|---|---|---|
| | 0 | 15 | 30 | 45 | 60 |
| Butadiene | 27.65 | 24.08 | 19.51 | 15.32 | 10.98 |
| Chlorobutenes | 0.45 | 5.5 | 11.36 | 17.66 | 24.08 |
| 3-Pentenoic Acid | 57.45 | 56.79 | 56.52 | 55.45 | 54.48 |
| Chlorovaleric Acid | 0.04 | 0.23 | 0.42 | 0.60 | 0.76 |

The Butadiene conversion after 60 Minutes was only 56%

EXAMPLE 4

The Fisher Porter Tube was charged with the following:

| Clorobutenes | 35 Grams |
|---|---|
| 3PA | 25 Grams |
| Water | 0.155 Gram |
| CuCl | 0.12 Gram |

The tube was then evacuated and then charged with:

| Butadiene | 19 ml (+ or −2 ml) |
|---|---|

The tube, stirred with a magnetic stirring bar, was then immersed in a cold water bath and pressured to 140 psi with HCl. The temperature was to be controlled at 50 degrees C. by adjusting the water temperature and level in the bath. However, the reaction rate was so fast that the temperature initially rose above the desired 50 degrees and peaked out at a temperature of 63 degrees C. and eventually was controlled at 50 degrees C. The temperature inside the tube was as follows:

| Time (Min) | Temperature (Deg C.) |
|---|---|
| 0 | 50 |
| 1 | 58 |
| 2 | 62 |
| 3 | 63 |
| 5 | 56 |
| 6 | 50 |

Samples were taken and analyzed with the following results expressed in weight percent:

|           | Time (min) |       |       |       |       |
|-----------|------|-------|-------|-------|-------|
|           | 0    | 2.5   | 5.0   | 7.5   | 10.0  |
| Butadiene | 17.70 | 6.38 | 1.29 | 0.51 | 0.43 |
| Chlorobutenes | 41.18 | 56.68 | 63.93 | 66.93 | 67.05 |
| Pentenoic Acid | 31.34 | 30.04 | 29.38 | 27.66 | 27.62 |
| Chlorovaleric Acid | 0.02 | 0.04 | 0.07 | 0.08 | 0.10 |
| Butadiene Conv | 0 | 62 | 92 | 97.3 | 97.7 |

The Butadiene conversion in Example 4 was higher after 2.5 minutes (62%) than the conversion after 60 minutes (56%) in Example 1. Thus the reaction rate was more than 24 times faster in Example 2 than in Example 1. The yield loss to ClVA was also significantly lower in Example 2.

EXAMPLE 5

Removal of Chlorovaleric Acid from 3PA

A 10 Plate, one inch Diameter Oldershaw Column, with a 500 Ml Pot was charged with 3PA containing some 3 & 4 chlorovaleric Acids (ClVA). A small amount of Toluene was also charged to allow removal of small amounts of HCl as a gas overhead while nitrogen was slowly added to the top plate of the Column.

The Still was quickly heated to reflux at 1 Atm., and samples taken from the Pot for analysis.

The Pot temperature was 197 degrees C. and the Head temperature was 110 degrees C. during the above test. The Head Pressure on the Column was then reduced to 100 mm Hg and 90% of the Pot Contents distilled over at a Reflux Ratio (L/D) of 1/1. The Still was shut down, and the Distillate and Pot contents analyzed. The analysis of the samples and the pot contents, in weight percent, are shown below:

| Time (min) | Chlorovaleric Acid |
|------------|---------------------|
| 0 | 2.52 |
| 20 | 0.45 |
| 40 | 0.15 |
| 60 | 0.07 |
| 90 | 0.04 |
| 12 | 0.02 |
| Distillate | <0.02 |
| Pot | 0.07 |

Examples 6 through 9 below demonstrate the reaction of 3-pentenoyl chloride and butadiene with water (and in some examples HCl and CuCl) to form 3-pentenoic acid and chlorobutenes.

EXAMPLE 6

Use of Stoichiometric Water

A 100 mL Hastelloy C autoclave was loaded with a solution containing:

18.28 gr. 3-pentenoyl chloride
8.4 gr. of butadiene
44.91 gr. of crotyl chloride The autoclave pressure was set to 300 psi with CO and then the system heated to 50 degrees C. Water (2.5 gr.) was added through an addition tube connected to the autoclave. Samples were removed every 30 minutes from the autoclave. The results are shown in Table 4.

EXAMPLE 7

Use of Excess Water

A 100 mL Hastelloy C autoclave was loaded with a solution containing:

14.74 gr. 3-pentenoyl chloride
6.69 gr. of butadiene
44.91 gr. of crotyl chloride The autoclave pressure was set to 900 psi with CO and then the system heated to 50 degrees C. Water (5 gr.) was added through an addition tube connected to the autoclave. Samples were removed every 30 minutes from the autoclave. The results are shown in table 4.

EXAMPLE 8

Use of Concentrated HCl

A 100 mL Hastelloy C autoclave was loaded with a solution containing:

14.10 gr. 3-pentenoyl chloride
6.10 gr. of butadiene
35.9 gr. of crotyl chloride The autoclave pressure was set to 300 psi with CO and then the system heated to 50 degrees C. Concentrated HCl (8.5 gr.) was added through an addition tube connected to the autoclave. Samples were removed from the autoclave at 15, 45, 60 90 and 120 minutes. The results are shown in table 4.

EXAMPLE 9

Use of Concentrated HCl and CuCl

A 100 mL Hastelloy C autoclave was loaded with a solution containing:

14.33 gr. 3-pentenoyl chloride
5.92 gr. of butadiene
45.0 gr. of crotyl chloride The autoclave pressure was set to 300 psi with CO and then the system heated to 50 degrees C. A solution containing 12 gr. of concentrated HCl and 0.452 gr. of CuCl was added through an addition tube connected to the autoclave. Samples were removed from the autoclave at 15, 45, 60 90 and 120 minutes. The results are shown in Table 4.

TABLE 4

| Example | Time (min) | BD (% Conv to chlorobutene) | 3PACl (mole %) | 3PA (mole %) | 3PAA (mole %) | ClVAl (mole %) |
|---------|------------|------------------------------|----------------|---------------|----------------|-----------------|
| 6 | 90 | 0 | 51.33 | 38.64 | 10.03 | 0 |
| 7 | 90 | 0 | 2.62 | 94.93 | 0 | 2.45 |
| 8 | 90 | 53.2 | 0 | 90.86 | 0 | 9.14 |
| 9 | 15 | 100 | 0 | 99 | 0 | 1 |

BD = 1,3-butadiene
CB = Chlorobutenes
3PACl = 3-pentenoyl chloride
3PA = 3-pentenoic acid
3PAA = 3-pentenoic acid anhydride
ClVAl = Chlorovaleric acid

EXAMPLE 10

Preparation of 3-pentenoyl chloride from chlorobutene and the simultaneous preparation of $C_{10}H_{11}O_4PdCl$ A 100 mL Hastelloy C autoclave was charged with 66.6 gr. of chlorobutene, 0.3 gr. of $C_4H_7PdCl$ the system closed and purged with CO. The CO pressure was set to 1000 psi, the system heated to 120° C. for 2 hours. The autoclave was cooled to 25° C., vented and the solution transferred under nitrogen to a glass distillation apparatus. A liquid sample analyzed by g.c. showed 23 mole % 3-pentenoyl chloride. The solution was distilled at atmospheric pressure until the pot temperature reached 140° C. The heels were cooled to room temperature and the green solids isolated. Yield: 0.15 gr. (32% yield based on palladium). The green solid was analyzed and found to have the formula $C_{10}H_{11}O_4PdCl$ and the following structure: gr. (32% yield based on palladium). The green solid was analyzed and found to have the formula $C_{10}H_{11}O_4PdCl$ and the following structure:

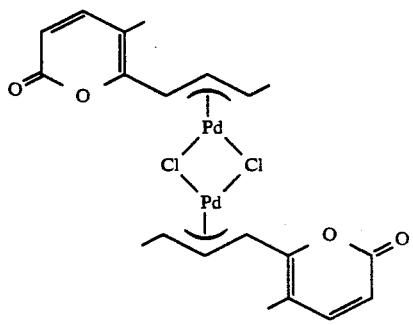

We claim:

1. A process for the preparation of 3-pentenoic acid which comprises:
   a) reacting a chlorobutene selected from the group consisting of 3-chloro-1-butene, and 1-chloro-2-butene, and carbon monoxide in the presence of 0.05 to 5 percent by weight of a palladium catalyst at a temperature between 90 and 190 degrees C. and at a carbon monoxide pressure of between 250 and 5,000 psig to form a reaction mixture containing 3-pentenoylchloride, carbon monoxide, 3-chloro-1-butene and 1-chloro-2-butene,
   b) separating carbon monoxide from the reaction mixture by heating the mixture at a temperature in the range of 100 to 140 degrees C. at a pressure of 25 to 1500 psig,
   c) separating a mixture containing 3-pentenoylchloride and chlorobutenes from the remaining portion of the reaction mixture by distillation, and simultaneously forming $C_{10}H_{11}O_4PdCl$,
   d) passing $C_{10}H_{11}O_4PdCl$ to step a) above,
   e) combining the separated mixture containing 3-pentenoylchloride and chlorobutenes with water, butadiene, and hydrochloric acid to form a mixture where the ratio of butadiene to pentenoylchloride is 1:1 to 6:1 and the molar ratio of water to 3-pentenoylchloride is 1:1 to 15:1, and reacting this mixture at a temperature in the range of about 0 degrees C. to 100 degrees C., and at a pressure of about 50 to 600 psig, and forming a two phase mixture comprising an organic phase containing 3-pentenoic acid, chlorovaleric acid, and additional chlorobutene selected from the group consisting of 3-chloro-1-butene and 1-chloro-2-butene, and an aqueous phase,
   f) separating the two phases and separating chlorobutenes from the organic phase by distillation and passing the chlorobutenes to step a) above,
   g) separating 3-pentenoic acid from the organic phase by distilling the mixture.

2. The process of claim 1 in which cuprous chloride is in the mixture formed in step e) and the copper content is in the range of 500 to 20000 ppm of the formed mixture.

3. The process of claim 1 in which 1 to 4% by weight water is added to the mixture remaining after step f).

4. A process for the preparation of 3-pentenoylchloride which comprises:
   a) reacting a chlorobutene selected from the group consisting of 3-chloro-1-butene and 1-chloro-2-butene, and carbon monoxide in the presence of 0.05 to 5 percent by weight palladium catalyst of formula $C_{10}H_{11}O_4PdCl$ at a temperature between 90 and 190 degrees C. and at a carbon monoxide pressure of between 500 and 5,000 psig to form a reaction mixture containing 3-pentenoylchloride, carbon monoxide, 3-chloro-1-butene and 1-chloro-2butene,
   b) separating carbon monoxide from the reaction mixture by heating the mixture at a temperature in the range of 100 to 140 degrees C. at a pressure of 25 to 1500 psig,
   c) separating a mixture containing 3-pentenoylchloride and chlorobutene from the remaining portion of the reaction mixture by distillation.

5. A process for the preparation of $C_{10}H_{11}O_4PdCl$ which comprises:
   a) reacting a chlorobutene selected from the group consisting of 3-chloro-1-butene and 1-chloro-2-butene, and carbon monoxide in the presence of 0.05 to 5 mole percent by weight palladium catalyst at a temperature between 90 and 190 degrees C. and at a carbon monoxide pressure of between 500 and 5,000 psig. to form a reaction mixture containing 3-pentenoylchloride, carbon monoxide, 3-chloro-1-butene and 1-chloro-2-butene,
   b) separating carbon monoxide from the reaction mixture by heating the mixture at a temperature in the range of 100 to 140 degrees C. at a pressure of 25 to 1500 psig,
   c) separating a mixture containing 3-pentenoylchloride and chlorobutene from the reaction mixture by distillation, and simultaneously forming $C_{10}H_{11}O_4PdCl$.

6. $C_{10}H_{11}O_4PdCl$ having the structural formula:

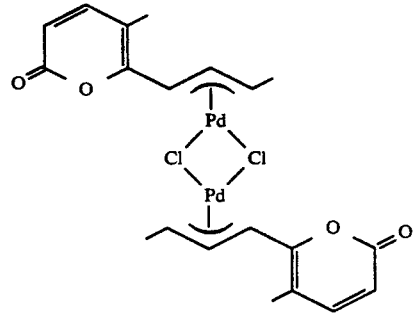

7. A process for the simultaneous preparation of 3-pentenoic acid, 3-chloro-1-butene and 1-chloro-2-butene which comprises:
   a) combining 3-pentenoylchloride with water, butadiene, and hydrochloric acid to form a mixture where the ratio of butadiene to pentenoylchloride is 1:1 to 6:1 and the molar ratio of water to 3-pentenoylchloride is 1:1 to 15:1, and reacting this mixture at a temperature in the range of about 0 degrees C. to 100 degrees C., preferably 30 to 50 degrees C., and at a pressure of about 50 to 600 psig to form a mixture comprising an organic phase containing 3-pentenoic acid, chlorovaleric acid, 3-chloro-1-butene and 1-chloro-2-butene, and an aqueous phase,
   b) separating the two phases and separating said chlorobutenes from the organic by distillation,
   c) separating 3-pentenoic acid from the organic phase by distilling the mixture.

8. The process of claim 7 in which cuprous chloride is in the mixture formed in step a) and the copper content is in the range of 500 to 20000 ppm of the formed mixture.

9. The process of claim 7 in which 1 to 4% by weight water is added to the mixture remaining after step b).

10. A process for the preparation of 3-pentenoic acid which comprises:
   a) reacting a chlorobutene selected from the group consisting of 3-chloro-1-butene, and 1-chloro-2-butene, and carbon monoxide in the presence of 0.05 to 5 percent by weight of a palladium catalyst at a temperature between 90 and 190 degrees C. and at a carbon monoxide pressure of between 250 and 5,000 psig to form a reaction mixture containing 3-pentenoylchloride, carbon monoxide, 3-chloro-1-butene and 1-chloro-2-butene,
   b) combining the reaction mixture with water, butadiene, and hydrochloric acid to form a mixture where the ratio of butadiene to pentenoylchloride is 1:1 to 6:1 and the molar ratio of water to 3-pentenoylchloride is 1:1 to 15:1, and reacting this mixture at a temperature in the range of about 0 degrees C. to 100 degrees C., and at a pressure of about 50 to 600 psig to form a mixture comprising an organic phase containing 3-pentenoic acid, chlorovaleric acid, and additional chlorobutene selected from the group consisting of 3-chloro-1-butene and 1-chloro-2-butene, and an aqueous phase,
   c) separating said additional chlorobutenes from the organic phase by distillation and passing the chlorobutene to step a) above,
   d) separating 3-pentenoic acid from the organic phase by distilling the mixture,
   e) extracting the catalyst from the aqueous phase with an organic solvent and passing the extract to step a) above.

11. The process of claim 10 wherein the organic solvent used in step e) is selected from 3-chloro-1-butene, 1-chloro-2-butene or mixtures thereof.

12. The process of claim 10 in which cuprous chloride is in the mixture formed in step b) and the copper content is in the range of 500 to 20,000 ppm of the formed mixture.

13. The process of claim 1 in which 1 to 4% by weight water is added to the mixture remaining after step c).

* * * * *